United States Patent [19]

Walters

[11] 4,421,736
[45] Dec. 20, 1983

[54] SUSTAINED RELEASE DIETHYLPROPION COMPOSITIONS

[75] Inventor: Eugene L. Walters, Cincinnati, Ohio

[73] Assignee: Merrel Dow Pharmaceuticals Inc., Cincinnati, Ohio

[21] Appl. No.: 379,848

[22] Filed: May 20, 1982

[51] Int. Cl.³ .................. A61K 9/52; A61K 9/56; A61K 9/62

[52] U.S. Cl. .................. 424/19; 424/20; 424/21; 424/22; 424/37; 424/38; 424/35

[58] Field of Search .................. 424/19–22, 424/35, 37, 38

[56] References Cited

U.S. PATENT DOCUMENTS

| | | | |
|---|---|---|---|
| 3,001,910 | 9/1961 | Schutte | 167/55 |
| 3,065,143 | 11/1962 | Christenson et al. | 424/19 |
| 3,119,742 | 1/1964 | Heimlich et al. | 424/20 |
| 3,147,187 | 9/1964 | Playfair | 424/19 |
| 3,297,804 | 1/1967 | Iwamoto et al. | 424/37 |
| 3,344,029 | 9/1967 | Berger | 424/19 |
| 3,374,146 | 3/1968 | Blicharz et al. | 424/19 |
| 3,427,378 | 2/1969 | Henderson et al. | 424/14 |
| 3,492,397 | 1/1970 | Peters et al. | 424/20 |
| 3,670,065 | 6/1972 | Eriksson et al. | 424/19 |
| 4,126,672 | 11/1978 | Sheth et al. | 424/22 |
| 4,132,753 | 1/1979 | Blichare et al. | 424/19 |

FOREIGN PATENT DOCUMENTS 109438  1/1940  Australia .................. 424/20

*Primary Examiner*—Shep K. Rose
*Attorney, Agent, or Firm*—William J. Stein; Gary D. Street; Raymond A. McDonald

[57] ABSTRACT

Sustained release formulations for the anorectic agent, diethylpropion hydrochloride, are disclosed which are suitable for use in capsules.

6 Claims, No Drawings

SUSTAINED RELEASE DIETHYLPROPION COMPOSITIONS

BACKGROUND OF THE INVENTION

Diethylpropion hydrochloride, 1-phenyl-2-diethylamino-1-propanone hydrochloride is a known sympathomimetric agent which is highly useful for its anorexigenic properties. This compound and its properties are fully described in U.S. Pat. No. 3,001,910, and has been marketed for a number of years in tablet form as Tenuate ®, diethylpropion hydrochloride USP (Merrell Dow Pharmaceuticals Inc.), and also as a sustained release tablet, Tenuate Dospan ®, diethylpropion hydrochloride USP for the treatment of obesity.

It would be highly desirable to provide a diethylpropion hydrochloride formulation that would be suitable for use with either hard or soft shell gelatin capsules. Not only is there a preference in some patients for a drug to be administered in capsule form, but capsule formulations generally permit the drug to be administered in a more concentrated form having fewer excipients added thereto. Furthermore, capsule formulations are tasteless, easily administered and generally provide greater stability as compared with tablet formulations inasmuch as such formulations remain free from those variables introduced during the compression of tablets. Moreover, capsule formulations are generally free from various additives such as stearates, binders, dispersing agents, coatings and flavoring agents that are generally required in tablet formulations.

The search for an alternative dosage unit form for diethylpropion hydrochloride, more particularly a sustained release capsule dosage unit form has not been without difficulty. Quite unexpectedly, the uncompressed tablet granulation, when placed in either a hard or soft shelled gelatin capsule, did not produce the desired sustained release effect. After many unsuccessful attempts, I have discovered a stable formulation of diethylpropion hydrochloride which is suitable for administration via either hard or soft shelled gelatin capsules, which is stable, and which will provide the critical timed release pattern that has been approved by the Food and Drug Administration.

SUMMARY OF THE INVENTION

This invention relates to novel sustained release pharmaceutical formulations containing diethylpropion hydrochloride. More particularly, this invention relates to sustained release formulations of diethylpropion hydrochloride which are suitable for use in capsules. Still more particularly the formulations described and claimed herein possess timed release characteristics such that appetite control can be effectively regulated via the administration of only one capsule per day.

DETAILED DESCRIPTION OF THE INVENTION

In accordance with this invention there are provided sustained release formulations of diethylpropion hydrochloride that are suitable for use with either hard or soft gelatin capsules. Basically these formulations require that the diethylpropion hydrochloride be uniformly dispersed in a matrix in which the drug is insoluble. Moreover, this matrix must be a hydrophobic material which is less soluble than the drug in depot fluids. Unfortunately, however, the use of such a drug matrix per se results in too rapid a release of the drug.

I have discovered that if the wax matrix is granulated and the individual granules are surrounded by a hydrophilic gum, a timed-release pattern can be obtained which provides a constant and uniform release of diethylpropion hydrochloride over an eight hour period. A hydrophilic gum, such as hydroxypropyl methylcellulose, has been found to be useful in this regard. More particularly, the hydrophilic gum, hydroxypropyl methylcellulose (4000 CPS-K4M) provides excellent results when used in combination with the wax matrix granules as described below.

If diethylpropion hydrochloride is used in combination with a hydrophilic gum, again the drug is released too rapidly. However, when wax matrix granules containing diethylpropion hydrochloride are prepared and the granules surrounded by hydrophilic hydroxypropyl methylcellulose gum, the desired timed-release effect is obtained.

It is thought that the hydrophilic gum functions by hydrating and swelling when in contact with depot fluids. In so swelling a relatively water impermeable barrier is formed around the wax matrix granules which prevents rapid dissolution. As the mucilagenous gum slowly becomes worn or dissolved away by the motion of the capsule mass in the gastro-intestinal tract, a fresh surface of the granulated wax matrix containing drug substance is constantly being exposed, thereby permitting the drug to be leached out at a slow but nevertheless constant rate.

For purposes of this application the wax matrix is defined as a uniform dispersion of diethylpropion hydrochloride in a solid hydrophobic material in which the drug is essentially insoluble. Among the hydrophobic materials that have been found to be useful are natural and synthetic waxes, resins and plastics. Of these ordinary paraffin, and more particularly, a mixture of paraffin and castor wax is preferred. Preferably, a mixture of 3 parts by weight of paraffin and one part by weight of castor wax is employed. Castor wax is a commercially available hydrogenated castor oil.

In order to prepare the wax matrix, diethylpropion hydrochloride is uniformly dispersed in the molten paraffin/castor wax mixture and allowed to solidify. The solid wax matrix is ground cryogenically, preferably using liquid nitrogen, and screened to form granules. Dissolution of the diethylpropion hydrochloride in depot fluids is dependent, among other things, upon the pore size and distribution of diethylpropion hydrochloride in the wax matrix. This, in turn, is determined by such factors as the concentration of the drug, the hydrophobicity of the external phase and the final screened size of the matrix particles. Preferably, the wax matrix particles contain about 3 parts by weight of diethylpropion hydrochloride, about 1 part by weight of hydrogenated castor oil and about 3 parts by weight of paraffin.

The wax matrix granules are then mixed with a hydrophilic gum, such as hydroxypropyl methylcellulose. The hydroxypropyl methylcellulose comprises from about 30 to 40% by weight of the total composition. Preferably, a hydroxypropyl methylcellulose (4000 CPS-K4M) is employed (Dow Chemical Company). This product represents a mixed hydroxypropyl methylcellulose ether having a relatively high viscosity and low thermal gelation characteristics.

In addition to the hydrophillic gum, various excipients can also be blended in with the wax matrix granules. In this regard, tartaric acid is favorably employed as a stabilizing agent for the diethylpropion hydrochloride. Preferably, the amount of tartaric acid employed represents from about 8 to 10% of the total weight of the finished pharmaceutical composition.

Dyes and granulation lubricants can be gainfully employed. Suitable lubricants include stearic acid and hydrogenated peanut oil and/or combinations of both. Such excipients represent from 2 to 4% by weight of the finished pharmaceutical composition.

The foregoing invention can be more particularly illustrated by means of the following Examples, but is not necessarily limited thereto.

EXAMPLE 1

Preparation of a Sustained Release Capsule Formulation

Seven hundred and fifty thousand two-piece hard shell capsules suitable for oral use are prepared using the following ingredients:

|  | Amount |
| --- | --- |
| Diethylpropion hydrochloride | 59.06 kg |
| Tartaric acid | 22.50 kg |
| Red dye FD & C #3 | 4.50 kg |
| Paraffin | 56.25 kg |
| Hydrogenated castor oil | 18.75 kg |
| Hydroxypropyl methylcellulose (4000 CPS-K4M) | 85.80 kg |
| Stearic acid | 3.75 kg |
| Hydrogenated peanut oil | 3.75 kg |

The diethylpropion hydrochloride (including manufacturing overage) is blended with approximately 0.6 kg of Tartaric acid and screened using a No. 20 screen. The paraffin is melted and added to the diethylpropion hydrochloride/tartaric acid blend and mixed well to form a wax matrix. The hydrogenated castor oil is melted and added with stirring to the wax matrix. The molten wax matrix is poured onto trays to harden, broken up and placed in a freezer overnight using closed containers with polyethylene bag liners in order to avoid excess exposure to moisture. The wax matrix is ground using liquid nitrogen through a Fitzmill grinder (#2A screen) and the wax matrix granules allowed to warm to room temperature in lined closed containers, so as to minimize exposure to moisture.

The so prepared diethylpropion hydrochloride wax matrix granules, the remainder of the tartaric acid, red dye and the hydroxypropyl methylcellulose are placed in a V-blender and thoroughly mixed. The stearic acid and hydrogenated peanut oil lubricants are screened (#30 screen), added to the above mixture and mixed well in a V-blender.

The resulting mixture is used to fill 750,000 capsules of the appropriate size. Each capsule contains approximately 75 mg of diethylpropion hydrochloride and has a net fill weight of 340 mg.

EXAMPLE 2

Preparation of Additional Sustained Release Capsule Formulations

Following essentially the same procedures as in Example 1, the following compositions were prepared on a smaller scale.

|  | Amount (gms) | | |
| --- | --- | --- | --- |
|  | 1 | 2 | 3 |
| Diethylpropion HCl | 78.25 | 78.25 | 78.25 |
| Paraffin | 50.00 | 90.00 | 50.00 |
| Hydrogenated castor oil | 50.00 | 10.00 | 25.00 |
| Tartaric Acid | 30.00 | 30.00 | 30.00 |
| Red FD & C #3 | 6.00 | 6.00 | 6.00 |
| Hydroxypropyl methylcellulose (4000 CPS - K4M) | 114.40 | 114.40 | 139.40 |
| Stearic acid | 5.00 | 5.00 | 5.00 |
| Hydrogenated peanut oil | 5.00 | 5.00 | 5.00 |

EXAMPLE 3

Dissolution Rates for Sustained Release Formulations

Dissolution profiles for three batches of diethylpropion capsules, prepared in accordance with the procedure of Example 1, were pooled by values at the 1st, 3rd, 5th and 7th hours. Data pooled represent the initial values and results at 1 and 3 months stability at room temperature, and at 3 months stability for temperatures at 37° C. and 40° C. Statistical analyses are determined for each set of pooled data for mean recovery, standard deviation, relative deviation and 99% and 95% confidence levels (C.L.). The column entitled "NDA Ranges" indicates the dissolution rate approved by the Food and Drug Administration for a sustained release formulation of diethylpropion hydrochloride. Dissolution ranges are determined in accordance with the standard procedure set forth in the United States Pharmacopeia, Vol. XX, pp. 959 (1980) using a USP rotating basket assembly at a speed of 100 rpm and a temperature of 37° C. using Simulated Gastric Fluid.

| | DISSOLUTION PROFILE-POOLED DATA | | | | | | |
| --- | --- | --- | --- | --- | --- | --- | --- |
| Hours | Mean Recovery (mg) | Std. Dev. mg | Relative Std. Dev. (%) | *No. Aberrant Values | 95% C.L. mg | 99% C.L. (mg) | NDA Ranges (mg) |
| 1st | 25.5 | 2.0 | 7.85 | 0 | 21.6–29.4 | 20.3–30.7 | 20–32 |
| 3rd | 52.6 | 3.3 | 6.29 | 3-high | 46.1–59.1 | 44.1–61.1 | 42–60 |
| 5th | 65.3 | 3.3 | 5.00 | 0 | 58.8–71.1 | 56.8–73.7 | 52–78 |
| 7th | 70.8 | 2.9 | 4.05 | 4-low | 65.1–76.2 | 63.4–78.2 | 66–84 |

*There were seven aberrant data values in the 552 values entered in the analysis.

I claim:

1. A sustained release pharmaceutical composition which comprises a capsule filled with granules of a wax matrix surrounded by a hydrophilic gum wherein the wax matrix consists essentially of 3 parts by weight of diethylpropion hydrochloride embedded in a mixture of 1 part by weight of hydrogenated castor oil and 3 parts by weight of paraffin, and wherein the surrounding hydrophilic gum consists essentially of from 4 to 5 parts by weight of a hydroxypropyl methylcellulose and from 1 to 1.5 parts by weight of tartaric acid.

2. A composition according to claim 1 wherein the hydrophilic gum is hydroxypropyl methylcellulose, 4000 CPS-K4M.

3. A composition according to claim 1 wherein the wax matrix represents from 50 to 60% by weight of the total composition.

4. A composition according to claim 1 wherein the hydrophilic gum represents from 30 to 40% by weight of the total composition.

5. A composition according to claim 1 wherein 0.2 parts of stearic acid and 0.2 parts of hydrogenated peanut oil are added as lubricants.

6. A composition according to claim 1 wherein from 75 mg to 80 mg of diethylpropion hydrochloride is present.

* * * * *